(12) United States Patent
Lewis et al.

(10) Patent No.: US 7,607,776 B1
(45) Date of Patent: Oct. 27, 2009

(54) DIGITAL EYE BANK FOR VIRTUAL CLINIC TRIALS

(76) Inventors: James Waller Lambuth Lewis, 133 Woodmont Dr., Tullahoma, TN (US) 37388; Ming Wang, 1801 West End Ave., Suite 1150, Nashville, TN (US) 37203

(*) Notice: Subject to any disclaimer, the term of this patent is extended or adjusted under 35 U.S.C. 154(b) by 0 days.

(21) Appl. No.: 11/585,522

(22) Filed: Oct. 24, 2006

Related U.S. Application Data

(60) Provisional application No. 60/729,667, filed on Oct. 24, 2005.

(51) Int. Cl.
*A61B 3/14* (2006.01)
*A61B 3/10* (2006.01)

(52) U.S. Cl. .................. 351/206; 351/212

(58) Field of Classification Search .......... 351/200–246
See application file for complete search history.

(56) References Cited

U.S. PATENT DOCUMENTS

| | | | |
|---|---|---|---|
| 4,889,422 A * | 12/1989 | Pavlidis | 351/210 |
| 5,517,021 A * | 5/1996 | Kaufman et al. | 250/221 |
| 5,649,061 A * | 7/1997 | Smyth | 706/16 |
| 2007/0066916 A1 * | 3/2007 | Lemos | 600/558 |

* cited by examiner

*Primary Examiner*—Mohammed Hasan
(74) *Attorney, Agent, or Firm*—Jason L. Hornkohl; Hornkohl Intellectual Property Law, PLLC

(57) ABSTRACT

A digital eye data bank contains digital eye information concerning a plurality of different eyes in the form of schematic eye models. Each model contains a quantitative and qualitative description of the optical performance of a human eye that can be used to simulate the eye's optical performance. Each schematic eye model is associated with at least one of an age, race, gender, geographic residence, or medical diagnosis of a group of individuals. The digital eye data bank also contains personal information such as body height, weight, education background, and physical, chemical, and mental status that may correspond to an eye condition associated with the eye model. The digital eye data bank is used to evaluate the performance of ocular instruments through computer simulation and predict a measurement outcome among a population of subjects.

7 Claims, 3 Drawing Sheets

DIGITAL EYE BANK FOR VIRTUAL CLINIC TRIALS

This is a utility patent application that claims priority from Provisional Patent Application No. 60/729,667, filed Oct. 24, 2005, which is hereby incorporated by reference, for a "DIGITAL EYE BANK FOR VIRTUAL CLINIC TRIALS, OPTIMIZATION OF OPTICAL DESIGN, & MEDICAL TRAINING" for the invention by J. W. L. Lewis, Ph.D. of a "Digital Eye Bank for Virtual Clinic Trials."

BACKGROUND OF THE INVENTION

Technological advances have led to a variety of new optical devices being designed in recent years. The obvious importance and sensitivity of human eyes require that each of these devices be thoroughly tested and certified prior to the device's introduction to, and use by, the public at large. The optical performance of an optical instrument can be predicted to a high accuracy using sophisticated computer simulations that are currently available. In addition, digital and analytical models of eyes can be created that can be used to simulate the eyes' optical performance. Unfortunately, the eyes of individuals vary considerably, and procedures or instruments designed for a certain eye having a certain set of parameters can be completely unacceptable for a different eye type having a different set of parameters. Currently, clinical tests and trials are performed with human subjects in an attempt to account for these differences. Unfortunately, these tests are typically expensive, time consuming to perform and intrusive to the subjects upon which they are performed. Thus, prototypes of optical instruments are often tested on the design engineer's own eyes in the laboratory. In addition, many ocular instruments and procedures are designed to address particular optical problems that may be relatively rare. In such cases, it can be exceedingly difficult to find a suitable number of test subjects who have the desired optical condition and who are willing to subject themselves to the required tests and experiments. Therefore, what is needed is an improved method and apparatus for testing ocular instruments and performing ocular experiments.

BRIEF SUMMARY OF THE INVENTION

An embodiment of the present invention is directed toward a method of predicting an ocular instrument's performance when used on a population. In accordance with the method, a plurality of digital eye models are created by measuring a set of ocular parameters for a plurality of individuals' eyes. Each model preferably contains a quantitative and qualitative description of the optical performance of a human eye associated with the digital eye model and an age, race, gender, geographic residence and/or medical diagnosis of an individual associated with the digital eye model. The plurality of digital eye models are stored in a digital eye data bank and classified according to demographics and ocular parameters of the plurality of individuals from which the digital eye models were obtained. The plurality of digital eye models are selected to represent an expected distribution of eye types in the population or a subset of the population. The digital eye data bank is used to evaluate the ocular instruments through computer simulation and thereby predict the performance of the ocular instruments when used on the population. The ocular instruments include those instruments that analyze optical signals from human eyes for diagnosis or monitoring purposes in optometry and opthalmology. Examples of such instruments are an opthalmoscope, a retinoscope, a slit-lamp, a fundus camera, an ultrasound A- or B-scanner, a videokeratoscope, an eye tracking system, a telescope, a microscope, a binocular device and an accommodation detection system. The ocular instruments may also include instruments configured to measure glucose levels, oxygen levels, and hypertension and instruments that interact with human eyes when in operation.

Another embodiment of the present invention is directed toward a digital eye data base that includes a plurality of digital schematic eye models. Each of the digital schematic eye models includes ocular parameters related to an individual's or a statistics-based eye that can be used to simulate a performance of the eye. The digital eye models are searchable by at least one of a demographic group of the individual and an optical condition of the individual. The digital schematic eye models in the digital eye data base preferably include a variety of ocular parameters such as a customized corneal surface, two crystalline lens surfaces and locations, a retinal location and surface, and at least three ocular parameters that provide an equivalent optical performance of an eye represented by the digital schematic eye model. Wave front aberration data for the eye may also be included. The digital schematic eye model also preferably includes a measured physical dimension such as a one dimensional slice along the optical axis, visual axis, or line of sight, a two dimensional ocular cross section, or a three dimensional structure acquired by an ultrasound A-, or B-Scan, Orbscan, MRI, or other suitable instrument. In addition, the digital schematic eye models may further include retina surface data such as a fundus image covering a range of the field angle of an individual associated with the model, a spectroscopic property including wavelength- and direction-dependent scattering, reflection, transmission, or absorption for an eye associated with one of the eye models, or measured cellular properties including at least one of a density and distribution of different types of photo-receptors and a retina pigment of an eye. The eye model data is preferably stored in a standardized optical format such as ZEMAX®, Code-V®, Synopsis®, or Oslo® such that the digital eye data base's information can be directly utilized by standardized optical equipment. In addition, personal information relating to at least one of body height, weight, educational background, and physical, chemical, or mental status of an individual associated with each of the digital schematic eye models is stored in a file associated with each of the digital schematic eye models.

Yet another embodiment of the present invention is directed toward a digital eye data base that includes a plurality of digital eye models. Each of the digital eye models is based upon an eye of an individual and can be used to predict an optic performance of the individual's eye. Each digital eye model includes demographic information associated with the individual. A subset of the digital eye models can be selected based upon a specific abnormality or a physical, medical, or environmental condition of the individual's eye represented by the associated digital eye model. A normal or abnormal ocular parameter distribution function is preferably determined for the subset of digital eye models. The data base includes developed eye models in which abnormalities are synthesized and introduced into to a digital eye model to predict a visual performance of an eye associated with the digital eye model having the introduced abnormality. The abnormality may be keratoconus on a cornea, a cataract in a crystalline lens, floaters in vitreous humor, and retinoblastoma or diabetic retinopathy on a retina. The abnormality factors are preferably selected according to a population distribution function acquired from statistical data used to construct a developed eye model corresponding to the abnormality. The data base is used to perform optical simulation of measurements by ocular instruments using the digital eye models to evaluate both the detection sensitivity and specificity of the ocular instruments.

DETAILED DESCRIPTION OF THE INVENTION

The present invention is directed toward a virtual eye data bank and a method of evaluating ocular instruments and improving their optical design using the data bank. The data bank contains a number of individual eye models for different eye types. The eye models preferably contain data related to the corneal surface, crystalline lens surfaces, retinal location and the eye's refractive prescription. In addition, each individual model is specific to, and classified by, race, gender, age, area of residence, refractive prescription and measured corneal topography. A variety of widely used optical design and analysis codes such as ZEMAX®, Code-V®, Synopsis® and/or Oslo® can be used to construct the eye models stored in the digital eye databank. The intraocular parameters are determined with the computer code for each individual eye. Preferably, $2^{nd}$ order and higher aberrations are measured for each eye represented in the digital eye data bank. The individual eye models can be used to test ocular instruments in a virtual environment on different types of eyes from a variety of different demographic groups.

Figure 1:
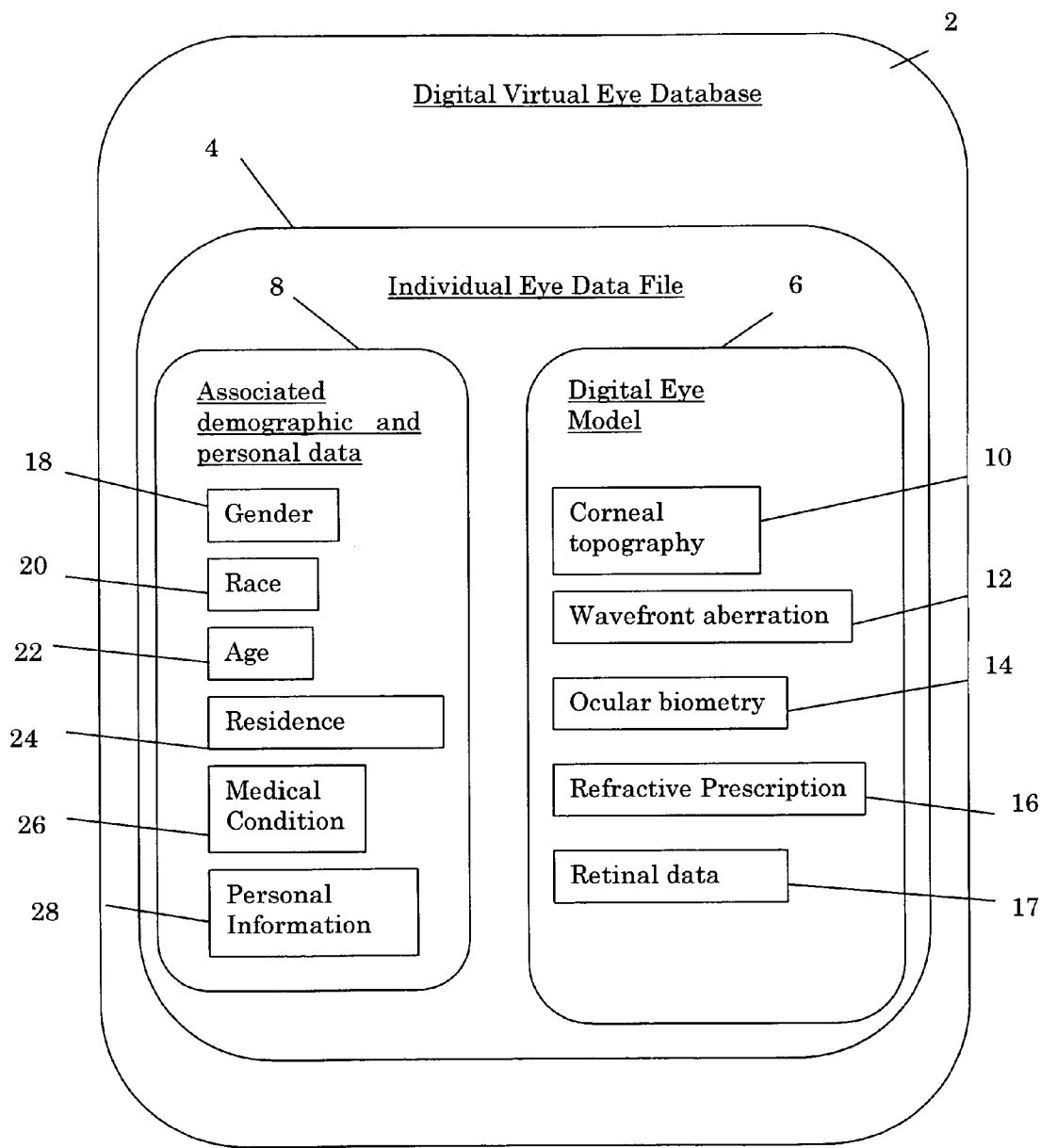
FIG. 1 is a block diagram of a digital eye data bank constructed in accordance with an embodiment of the present invention.

Referring now to FIG. 1, a block diagram of a digital eye data base constructed in accordance with an embodiment of the present invention is shown. The data base 2 consists of a series of individual virtual eye digital data files 4 that each has a digital eye model 6 and associated demographic and personal information data file 8. The digital eye model 6 includes schematic eye models for a plurality of individuals wherein each model contains a quantitative and qualitative description of the optical performance of the human eye associated with the schematic eye model. More particularly, the digital eye model 6 includes a digital representation of an individual's eye that is based upon measured eye parameters such as corneal topography 10, wave front aberration 12, the distance to, and thickness of, a set of optical elements or the ocular biometry 14 found in the individual's eye, the individual's refractive prescription 16 and retinal data 17. The refractive prescription 16 preferably includes at least data related to spherical refraction, cylindrical refraction, and astigmatism axis. The retinal data 17 preferably includes 2-dimensional retinal surface data such as a fundus image covering a range of field angle for an individual associated with the model and a surface scattering, reflecting, and transmission property that is wavelength- and direction-dependent. The retinal data may also include both retina pigment and measured cellular properties such as density and distribution of different types of photo-receptors of an eye associated with the prescribed schematic eye model. While the digital eye model 6 is shown containing a specific set of eye parameters, those skilled in the art will recognize that additional parameters such as the steering angles, accommodation amplitude, and pupil response could be added if needed to evaluate the performance of specific ocular instruments.

A commercial optics code such as Zemax™, can be used to generate the optical schematic digital eye models. Detailed optical eye modeling is possible when the measured corneal topography, wave front aberration and biometry of the individual's eye are obtained. Digital eye models can be used to assist ocular surgery, design personalized intraocular lens, spectacles, contact lens, and to predict both specific and statistical ocular responses to various stimuli. In addition, the models can be used in connection with computer simulations of instruments to predict the instruments' effectiveness and measurement results. Thus, the data base of digital eye models can be used to test and evaluate the performance of instruments on wide range of diverse subjects without actually performing any testing on actual patients.

Each digital eye model has an associated set of demographic and personal data 8 that can be searched to select digital eye models from individuals that have a certain set of characteristics. Preferably, the demographic data includes at least gender 18, race 20, age 22 and residence 24 of the individual from which the associated digital eye data was obtained. The personal information 28 includes information such as body height, weight, education background, and physical, chemical, and mental status that may be related to ocular conditions. The data base also preferably includes information related to any medical conditions 26 of the individual that may have an effect on their eyes performance. Additional demographic and personal data may be included in the data base 8 is desired.

While the eye data base 2 of FIG. 1 is shown as a single data base, sub-eye data bases containing information related to a specific abnormality or a specific physical, medical, or environmental condition may also be utilized in accordance with embodiments of the present invention. These sub-eye data banks are formed from a subset of the individual data files 4 stored in the digital eye data bank 2.

Figure 2:
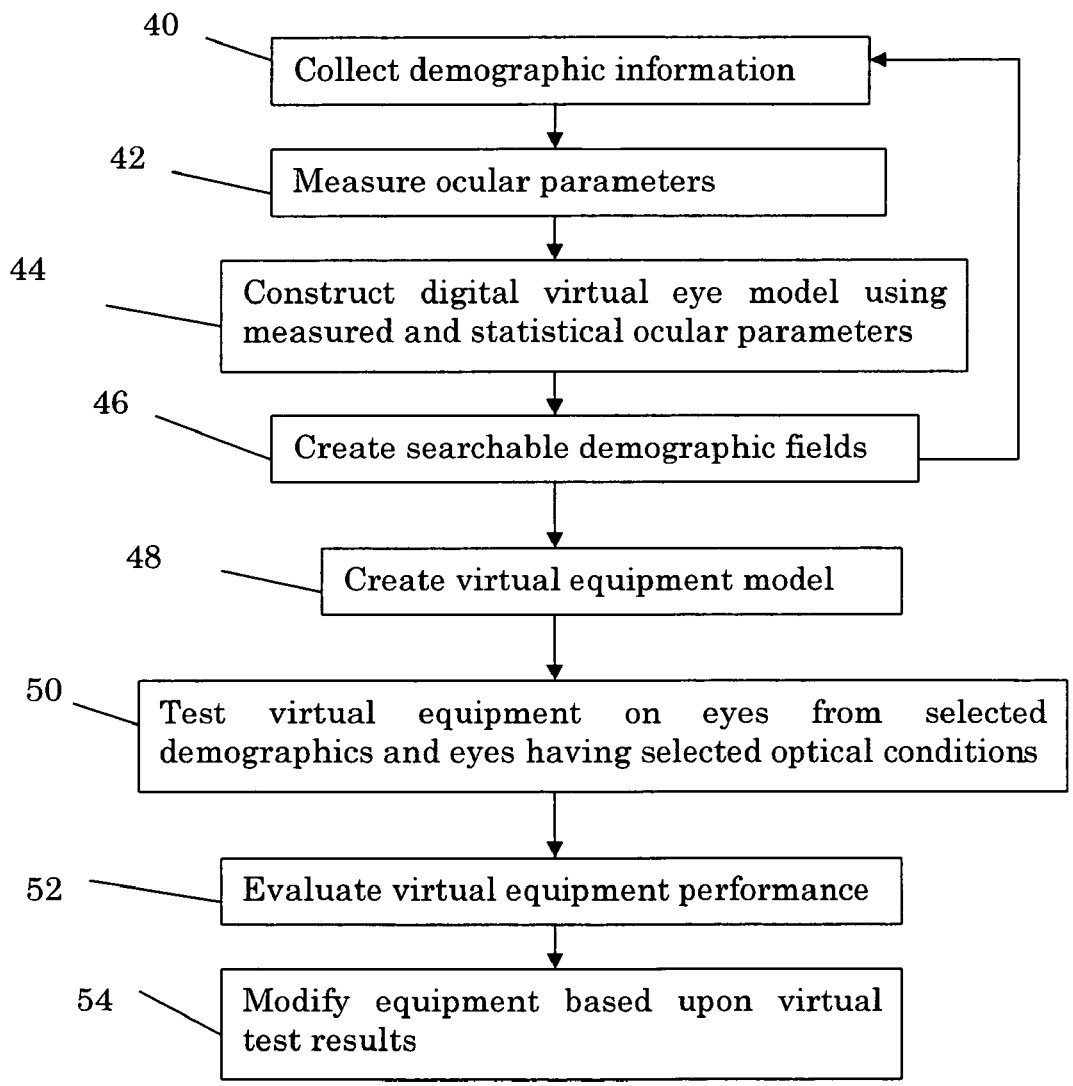
FIG. 2 is a flow chart of a method of compiling and using a digital eye data bank in accordance with an embodiment of the present invention.

Referring now to FIG. 2, a method of compiling and using a digital eye data bank in accordance with an embodiment of the present invention is shown. The method begins in step 40 with the collecting of demographic and personal information from a patient or subject that will be used to create a digital eye model. In step 42, measurements of the individual's eye's parameters are taken. As discussed in more detail herein, the digital eye data obtained from the measurements preferably include the anterior and posterior corneal topographies, wave front aberration and eye biometry data that can be obtained using commercial ophthalmic instruments. The digital eye data are then used, with additional ocular parameters acquired from statistics, to construct a digital eye model in step 44. The demographic data collected in step 40 are then organized into searchable fields that are associated with the digital eye model in step 46. The process of steps 40 through 46 is repeated until a large number of digital eye models for a variety of different demographics are obtained. In practice, the digital eye data bank will be an ongoing endeavor that continually gathers and compiles additional eye data. Once the data base has been created, a computerized virtual equipment model of an ocular instrument to be evaluated using the digital eye databank is created in step 48. In step 50, a virtual test of the equipment is performed using digital eye models from selected demographics and eyes having selected optical conditions. The equipment's expected performance is then evaluated based upon the test results in step 52. Based upon the evaluation, alterations to the equipment can be made as deemed appropriate.

Digital eye models can be altered in predetermined ways to represent ocular abnormalities. Thus, eye models from a particular demographic can be altered to include a particular abnormality such as a posterior polar cataract such that no actual eye data from individuals in the demographic having the abnormality are required. The data base may include these developed eye models in which abnormalities are synthesized and introduced into a digital eye model to predict a visual performance of an eye associated with the digital eye model having the introduced abnormality. The abnormality may be keratoconus on a cornea, a cataract in a crystalline lens, floaters in vitreous humor, and/or retinoblastoma on a retina. The abnormality factors are selected according to a population distribution function acquired from the same statistical data used to construct the developed eye model corresponding to the abnormality.

Figure 3:
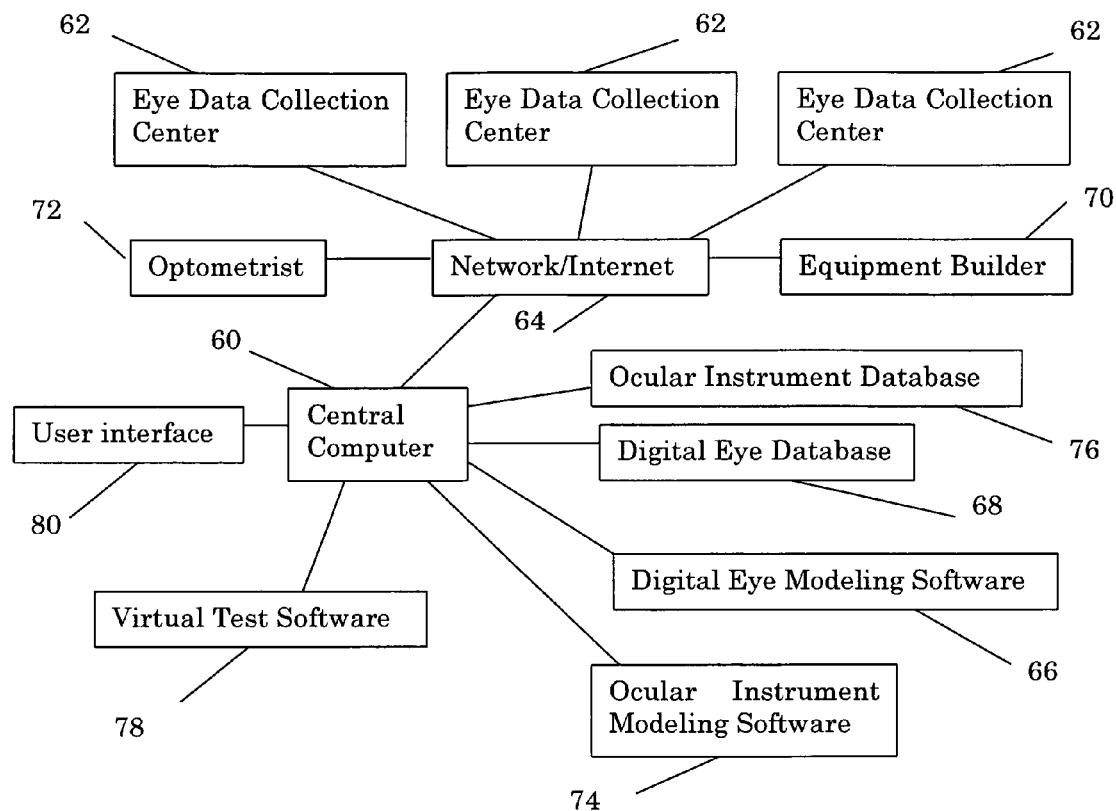
FIG. 3 is a block diagram of a system for compiling a digital eye data base in accordance with an embodiment of the present invention.

Shown in FIG. 3, is a block diagram of a system for compiling a digital eye data base in accordance with an embodiment of the present invention. The compiling of the digital eye data base is preferably managed by a central computer 60 that can be accessed by a system administrator through a user interface 80. The central computer 60 communicates with a plurality of eye data collection centers 62 through a network 64 such as the Internet. The eye data collection centers 62 can be optometrist offices, eye surgery centers, research facilities, or similar facilities that are in a position to measure eye parameters and record associated demographic data. The collected eye data is then provided to the central computer 60 through the network 64. The central computer 60 provides the data received from the collection centers 62 to digital eye modeling software 66 that creates a digital virtual eye schematic based upon the measured eye data as discussed herein. Alternatively, the eye modeling software may be maintained at the collection center 62, and the digital virtual eye data may be provided directly to the central computer 60 from the collection centers 62. The digital virtual eye model data is then stored in the digital eye data base 68 for later reference. The digital eye data base 68 preferably includes a customized corneal surface, two crystalline lens surfaces and locations, a retinal location and surface, and at least three ocular parameters for each eye that allow the central computer to predict a virtual simulation of the optical performance of the eye that is represented by the prescribed schematic eye model. The digital eye data are preferably stored in standardized optical format such as ZEMAX®, Code-V®, Synopsis®, or Oslo® such that the digital eye data bank information can be directly utilized by standardized optical equipment when needed.

The central computer 60 also receives and manages ocular instrument data. The ocular instruments include devices such as an opthalmoscope, a retinoscope, a slit-lamp, a fundus camera, an ultrasound A- or B-scanner, a videokeratoscope, an eye tracking system, a telescope, a microscope, a binocular device, an accommodation detection system, etc. The instrument data may be obtained from equipment builders 70, optometrists 72, collection centers 62, or any other available sources. The central computer 60 provides the instrument data to ocular instrument modeling software 74 that creates a virtual test equipment model that is stored in a virtual test equipment data base 76. Once the digital virtual eye data base 68 and virtual equipment data base 76 have been populated with data, the data are provided to virtual test software 78. The virtual test software 78 evaluates the ocular instrument's performance with respect to various different eye types from different demographics by performing virtual tests of the equipment with respect to the different eye types. For example, the optical simulation of measurements by the ocular instruments may be performed using the model eye data to evaluate a detection sensitivity of the ocular instruments or provide medical training. In addition, the instruments sensitivity and performance can easily be evaluated with respect to different demographics and ocular conditions without having to perform any actual test on a live test subject. Thus, a digital eye data bank constructed in accordance with an embodiment of the present invention significantly reduces the costs and time associated with evaluating ocular instruments.

Although there have been described particular embodiments of the present invention of a new and useful DIGITAL EYE BANK FOR VIRTUAL CLINIC TRIALS herein, it is not intended that such references be construed as limitations upon the scope of this invention except as set forth in the following claims.

We claim:

1. A method of predicting an ocular instrument's performance when used on a population, said method comprising:
    creating a plurality of digital eye models that can be used by a computer to simulate an eye's optic performance in a virtual environment by measuring a set of ocular parameters for plurality of individuals' eyes wherein each digital eye model includes data describing an individual eye's corneal surface and refractive prescription;
    storing said plurality of digital eye models in a digital eye bank wherein said plurality of digital eye models are classified according to demographics and ocular parameters of the plurality of individuals from which the digital eye models were obtained; and
    using said digital eye data bank and a digital model of said ocular instrument to evaluate said ocular instrument through computer simulation and thereby predict the performance of said ocular instrument when used on said population wherein said plurality of digital eye models represent an expected distribution of eye types in said population.

2. The method of claim 1 wherein said ocular instruments include instruments that deliver optical signals from or to human eyes for diagnosis, monitoring, or visual assistance purposes in optometry or opthalmology.

3. The method of claim 2 wherein said ocular instruments include at least one of an opthalmoscope, a retinoscope, a slit-lamp, a fundus camera, an ultrasound A- or B scanner, a videokeratoscope, an eye tracking system, a telescope, a microscope, a binocular device, and an accommodation detection system.

4. The method of claim 2 wherein said ocular instruments are configured to measure or monitor one of a glucose level, an oxygen level, drug usage level, temperature, and hypertension.

5. The method of claim 2 wherein said ocular instruments include an optical system that interacts with human eyes when in operation.

6. The method of claim 1 wherein said digital eye data bank comprises digital eye models for a plurality of individuals wherein each model contains a quantitative and qualitative description of the optical performance of a human eye associated with said digital eye model.

7. The method of claim 1 wherein each digital eye model is associated with at least one of an age, race, gender, geographic residence, genetic information, or medical diagnostic result of an individual associated with said digital eye model.

\* \* \* \* \*